(12) United States Patent
Baker

(10) Patent No.: US 8,603,549 B1
(45) Date of Patent: Dec. 10, 2013

(54) SYSTEMS AND METHODS FOR INHIBITING FORMATION OF STRETCH MARKS

(76) Inventor: Svetlana Baker, Highlands Ranch, CO (US)

( * ) Notice: Subject to any disclaimer, the term of this patent is extended or adjusted under 35 U.S.C. 154(b) by 0 days.

(21) Appl. No.: 13/481,495

(22) Filed: May 25, 2012

(51) Int. Cl.
*A61K 36/00* (2006.01)
*A61K 8/97* (2006.01)
*A61K 36/889* (2006.01)
*A61K 36/736* (2006.01)

(52) U.S. Cl.
USPC ............ 424/725; 424/402; 424/727; 424/735

(58) Field of Classification Search
None
See application file for complete search history.

(56) References Cited

U.S. PATENT DOCUMENTS

| | | |
|---|---|---|
| 5,468,495 A | 11/1995 | Kligman |
| 5,755,680 A | 5/1998 | Ghodsian |
| 6,120,887 A | 9/2000 | Werenicz et al. |
| 6,145,134 A | 11/2000 | Davis et al. |
| 6,319,957 B1 | 11/2001 | Ammar |
| 6,855,424 B1 | 2/2005 | Thomas et al. |
| 7,160,560 B2 | 1/2007 | Pinnell |
| 7,563,479 B2 | 7/2009 | Werenicz et al. |
| 7,615,016 B2 | 11/2009 | Baerthe et al. |
| 2006/0172022 A1* | 8/2006 | Szanzer .................. 424/757 |
| 2009/0137556 A1* | 5/2009 | Bonnichsen ............ 514/212.07 |
| 2010/0226947 A1* | 9/2010 | Theberge et al. ............ 424/401 |
| 2011/0230119 A1 | 9/2011 | Thompson |

* cited by examiner

*Primary Examiner* — Robert A Wax
*Assistant Examiner* — H. Sarah Park
(74) *Attorney, Agent, or Firm* — Kilpatrick Townsend & Stockton LLP

(57) ABSTRACT

According to the invention, a method for inhibiting the formation of stretch marks is disclosed. The method may include applying an oil to a portion of a person's body. The method may also include placing a non-absorbent film over the oil on the portion of the person's body. The method may further include securing the non-absorbent film to the person's body.

1 Claim, 5 Drawing Sheets

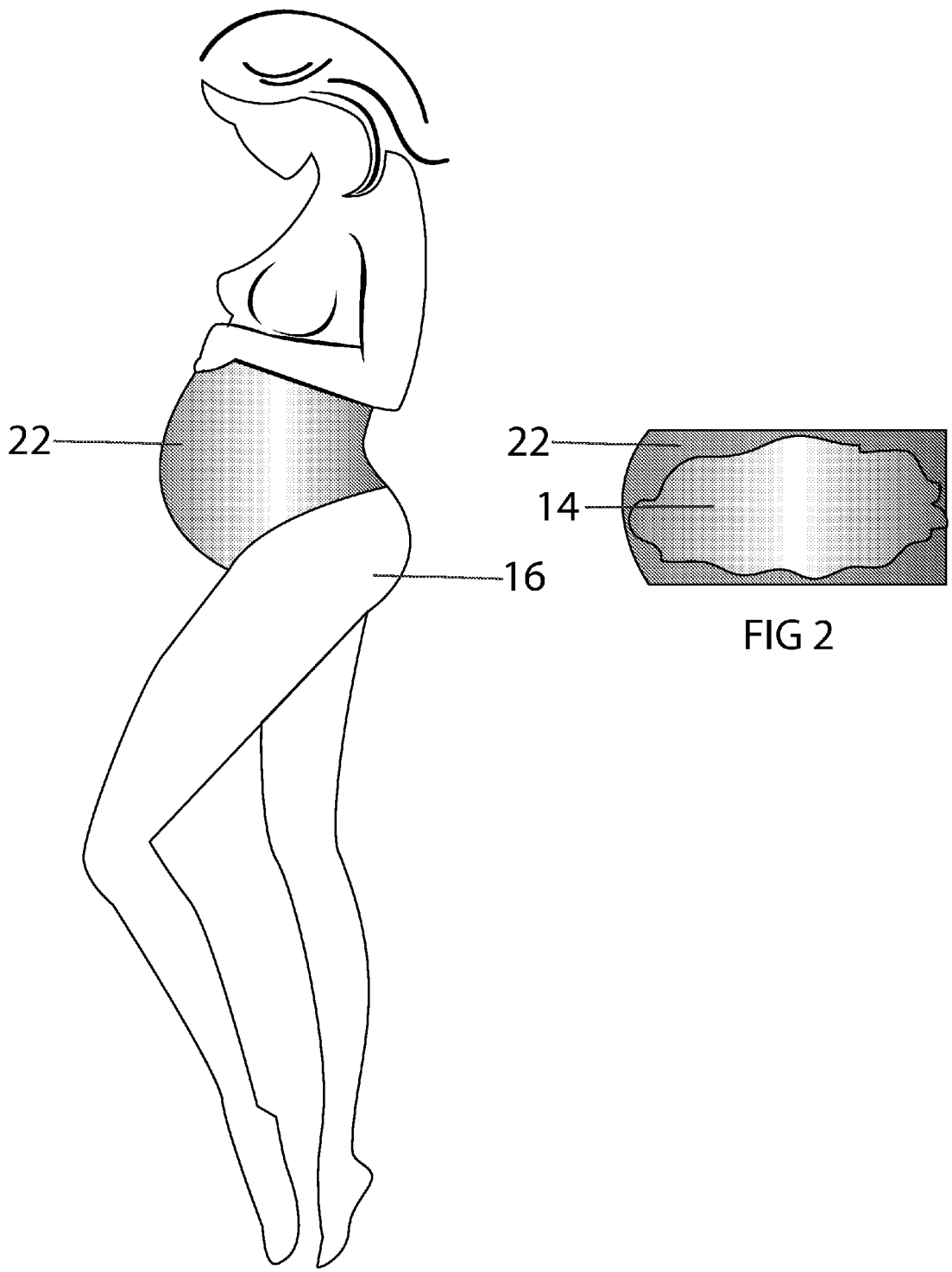

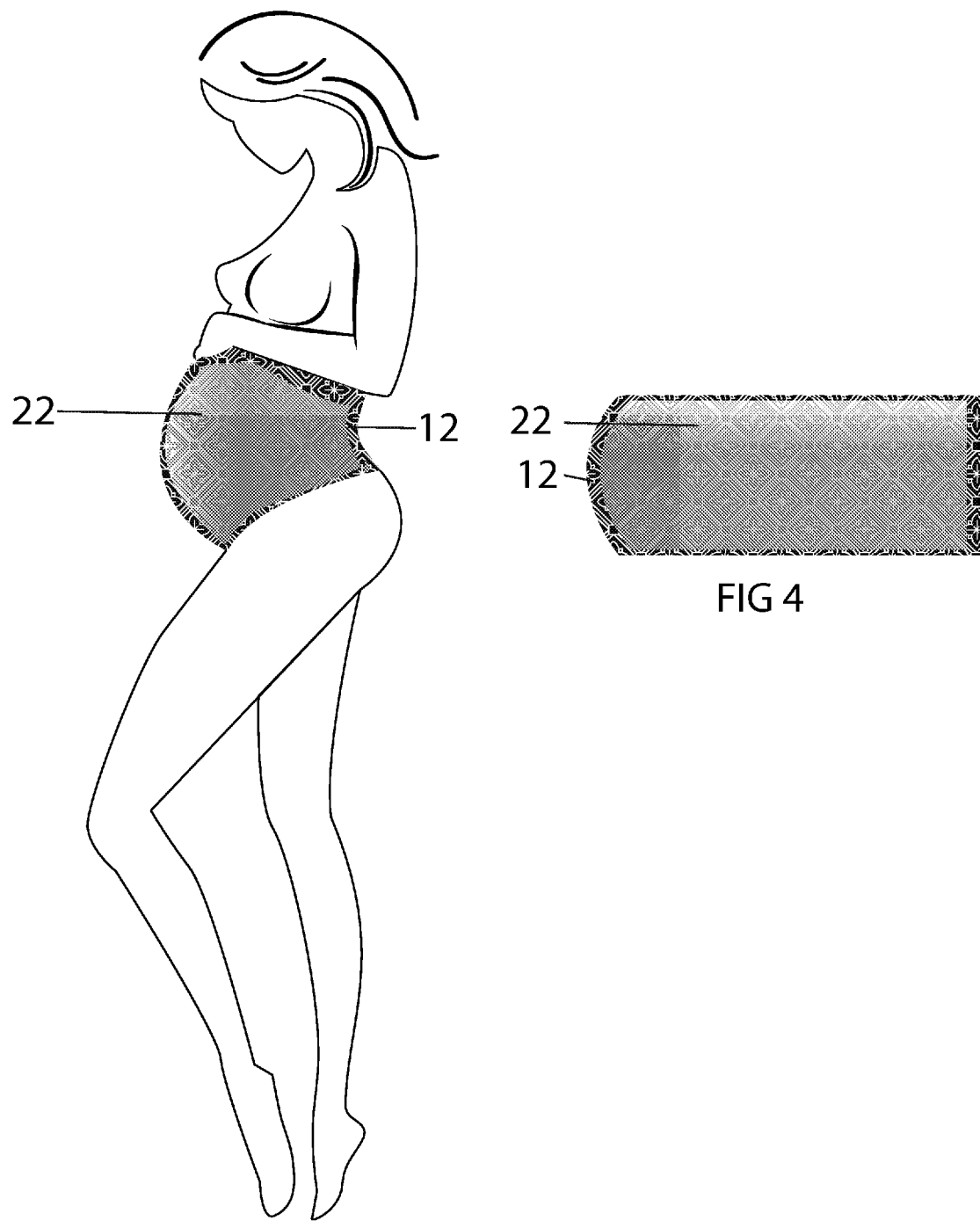

SYSTEMS AND METHODS FOR INHIBITING FORMATION OF STRETCH MARKS

BACKGROUND OF THE INVENTION

Since the beginning of time, women have worried and struggled with the possibility of getting stretch marks during pregnancy. Doctors often just advise women to lather up with lotion or oil and hope for the best. Unfortunately, up to 90% of women develop stretch marks during pregnancy. Many women long for an effective solution.

During a woman's pregnancy, the skin on the woman's abdomen is stretched to accommodate the growing baby. This causes the skin to tear, leaving a permanent, scar-like appearance known as stretch marks or striae of pregnancy.

While the benefits of keeping natural oils on the expanding abdomen during pregnancy has been promoted and encouraged by the medical community, the problem lies in the fact that women living in a modern society wear clothing that immediately absorbs almost any and all skin care products and oils that are applied. This negates any advantage that would have been achieved by potential absorption of the products/oils by the skin over time. Other ideas to treat and/or lessen the severity of stretch marks after they have already formed have been tried without much success.

BRIEF DESCRIPTION OF THE INVENTION

In one embodiment, a method for inhibiting the formation of stretch marks is provided. The method may include applying an oil to a portion of a person's body. The method may also include placing a non-absorbent film over the oil on the portion of the person's body. The method may further include securing the non-absorbent film to the person's body. In some embodiments, the non-absorbent film may have the oil pre-applied thereto.

In another embodiment, a method for inhibiting stretch marks is provided. The method may include applying an oil to a portion of a person's body. The method may also include placing a non-absorbent fabric over the oil on the portion of the person's body. The method may further include securing the non-absorbent fabric to the person's body.

In another embodiment, clothing for use in inhibiting stretch marks is provided. The clothing may include a garment made from a two layer fabric, where the two layer fabric is non-absorbent and is configured to retain an oil between the fabric and a person wearing the clothing in order to inhibit stretch mark formation.

BRIEF DESCRIPTION OF THE DRAWINGS

The present invention is described in conjunction with the appended figures:

FIG. 1 is a left side view of a pregnancy skin wrap of the a first embodiment as applied to a woman;

FIG. 2 is a front view of a pregnancy skin wrap of the first embodiment with ointment oil applied thereto;

FIG. 3 is a left view of the fabric cover of a second embodiment to be used in conjunction with the first embodiment of FIG. 1;

FIG. 4 is a front view of fabric cover of the second embodiment;

DETAILED DESCRIPTION OF THE INVENTION

Figure 5:
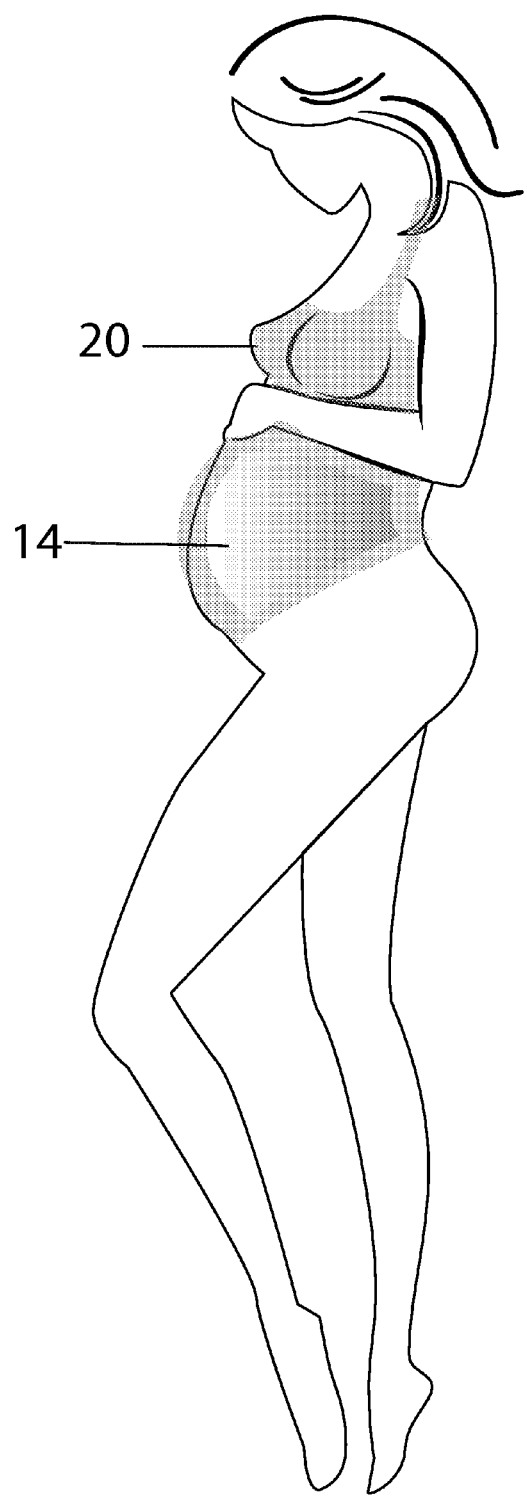
FIG. 5 is a left view of the pregnancy skin wrap clothing top of a third embodiment as applied to a woman.

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments. It will be understood by one of skill in the art that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, well known processes, structures, and techniques may be shown or discussed without unnecessary detail in order to avoid obscuring the embodiments.

In one embodiment, a pregnancy skin wrap is provided which acts as a barrier material between the skin and the clothing to prevent absorption by clothing of any applied beneficial oil applied to the pregnant woman. This may be combined with various ready to wear embodiments for everyday use starting at or around the second month of pregnancy, or possibly whenever a woman starts to show. These embodiments include pregnancy skin wrap clothing, such as tank tops or shorts, made from a non-absorbent two-layer fabric, including but not limited to polyester and polyurethane, which will prevent the absorption of beneficial ointment oil by clothing, the non-absorbent two-layer fabric. In other embodiments, the two layer fabric may be spandex/lycra/elastane and polyurethane. Other materials may be used in yet other embodiments.

In one embodiment the two-layer fabric may include a layer each of polyester and polyurethane (or other materials discussed herein or otherwise). In another embodiment, one layer may be polyester or polyurethane, while the other layer may be a mixture or weave of both polyester and polyurethane. In yet another embodiment, both layers will include a mixture or weave of both polyester and polyurethane. The two layers may also be woven together by various methods, including sewn together using polyester, polyurethane, and or some other thread material. Either material may be on either side of the fabric in relation to the wearer depending on the embodiment. In one embodiment, the polyurethane may be disposed on the side of the wearer while the polyester may be disposed on the outside of the clothing.

The pregnancy skin wrap clothing may also be worn in the postpartum period to aid the healing process to further prevent stretch marks when skin may be contracting back to pre-pregnancy shape. Embodiments of the invention may also improve the appearance of scars caused by medical intervention such as caesarian section incisions.

Another embodiment includes stretch mark prevention skin wrap clothing of many various types, also made from the non-absorbent two-layer fabric discussed above. These materials may prevent the absorption of beneficial oil by clothing, and thereby assist in preventing stretch marks in people such as bodybuilders or adolescents who are also prone to developing stretch marks. These embodiments can be used to aid in treatment of skin conditions such as eczema, psoriasis and other skin ailments. Another embodiment is a reusable and washable pregnancy skin wrap, made out of the same non-absorbent fabric. Yet another embodiment is a disposable pregnancy skin wrap and can be used in conjunction with a tailor made fabric cover to keep skin wrap in place. These embodiments may wrap partially or entirely around the torso or other portion of the affected person. Either the skin wrap or the fabric cover may secure around a portion of the user's body, possible with hook and loop fasteners (Velcro®), adhesive (one-time use or reusable), buckles, ties, etc.

Turning now to FIG. 1 and FIG. 2, a pregnancy skin wrap 22 is shown which is applied directly onto the clean abdomen of the pregnant woman 16 around the second month or whenever the woman starts to show. This acts as a barrier material and is preferably made from non-toxic film such as but not limited to polyethylene or polyurethane that is safe for contact with skin. The pregnancy skin wrap 22 can be worn as much as possible, and possibly at least overnight for eight hours. The pregnancy skin wrap 22 may be a daily disposable product. In one embodiment, the pregnancy skin wrap 22 may be placed around the pregnant woman's abdomen, around each side and covering the back. The ends of the pregnancy skin wrap 22 may meet together and be coupled such that it maintains its position around the woman.

An off the shelf or specially formulated ointment oil 14 may be either pre-applied to each disposable skin wrap, or applied prior to putting on disposable pregnancy skin wrap 22. The ointment oil 14 is preferable a blend of various natural oils. In one embodiment, the ingredients of the ointment oil 14 includes all natural ingredients such as but not limited to: olive oil, sweet almond oil, coconut oil, beeswax, avocado oil, cocoa butter, shea butter, tamanu oil, and natural vitamin E. The amount of each ingredient can vary, but in some embodiments may be proportionally equivalent to about 15 to 25% olive oil, about 15 to 25% sweet almond oil, about 15 to 25% coconut oil, about 10 to 18% beeswax, about 7 to 13% avocado oil, about 3 to 7% cocoa butter, about 3 to 7% shea butter, about 3 to 7% tamanu oil, and about 3% or less natural vitamin E. In one embodiment ointment oil 14 may be proportionally equivalent to about 20% olive oil, about 20% sweet almond oil, about 20% coconut oil, about 14% beeswax, about 10% avocado oil, about 5% cocoa butter, about 5% shea butter, about 5% tamanu oil, and about 1% natural vitamin E.

A tailor made fabric cover 12, as shown in FIG. 3 and FIG. 4, is designed to go over the disposable pregnancy skin wrap 22. There are various fabrics that comprise the fabric cover 12 including, but not limited to cotton, organic cotton, spandex, nylon, terry, lycra, polyester. The fabric cover 12 should be worn day and/or night to help keep the disposable pregnancy skin wrap in place 22 and/or provide an aesthetically pleasing appearance.

Figure 6:
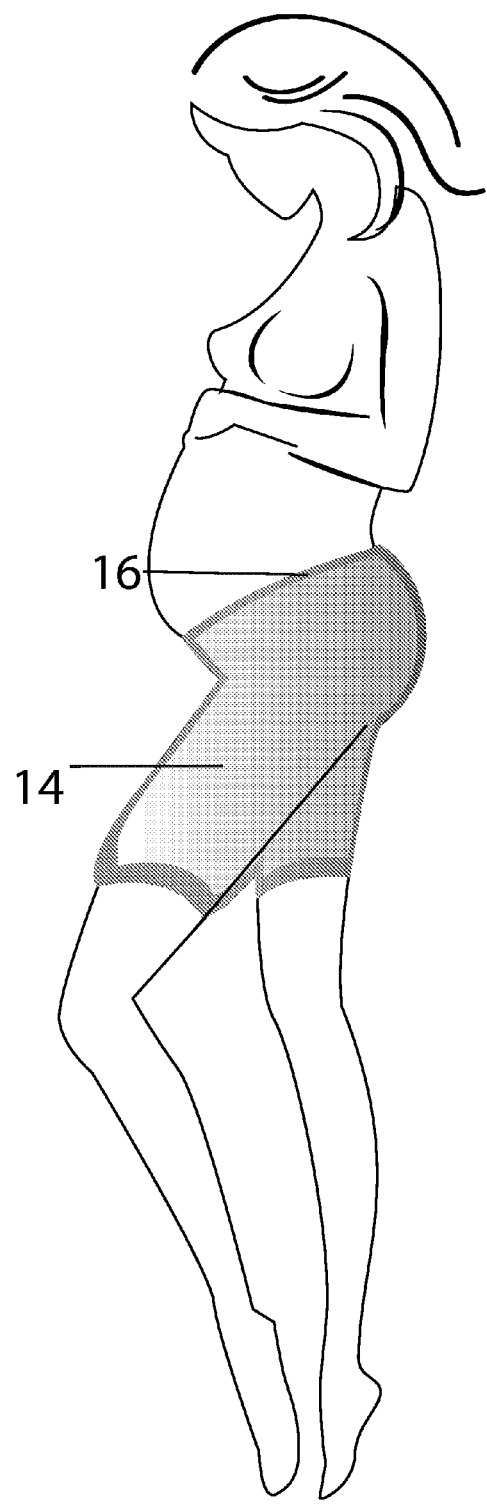
FIG. 6 is a left view of pregnancy skin wrap clothing shorts of the third embodiment as applied to a woman.

Pregnancy skin wrap clothing 20 of FIG. 5 is a further embodiment and will be made from a non-absorbent two-layer fabric, such as, but not limited to, polyester lined with polyurethane, which will prevent the absorption of beneficial oil by objects other than the affected skin. Pregnancy skin wrap clothing 20 will feature maternity clothing including, but not limited to maternity tank tops, maternity tee shirts, maternity dresses, maternity body suits, maternity shorts, and maternity pants. These clothing items may stretch to fit the user as their body changes shape during maternity. In FIG. 6, the pregnancy skin wrap clothing 16 illustrates maternity shorts. Ointment oil 14 is applied to skin prior to wearing pregnancy skin wrap clothing 20.

Figure 7:
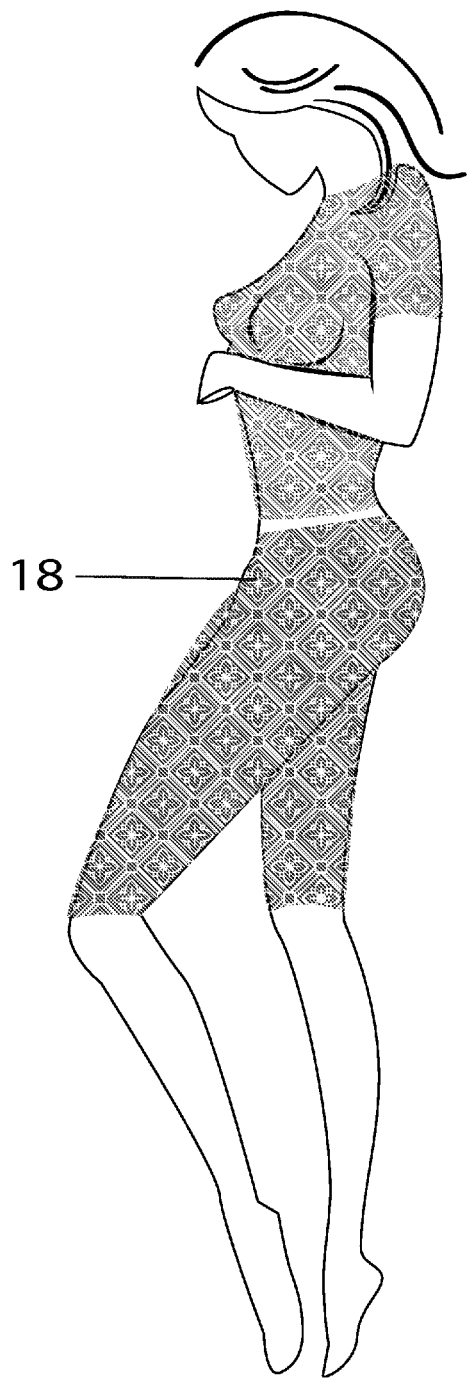
FIG. 7 is a front view of stretch mark prevention skin wrap clothing of the fourth embodiment.

Stretch mark prevention skin wrap clothing 18 of FIG. 7 is a further embodiment and may also be made from a non-absorbent two-layer fabric, such as but not limited to polyester lined with polyurethane, which will prevent the absorption of beneficial ointment oil 14. Stretch mark prevention skin wrap clothing 18 will include articles of clothing including shirts, tank tops, shorts, and pants. Ointment oil 14 is applied to skin prior to wearing stretch mark prevention skin wrap clothing 18. While clothing 18 is shown as a shirt and shorts in FIG. 7, other types of clothing as discussed above may also be employed.

Figure 8:
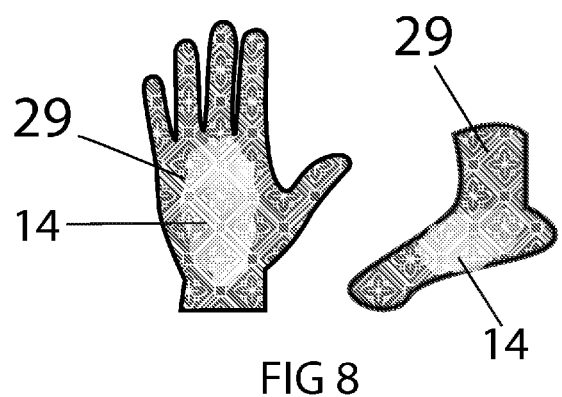
FIG. 8 is a front view of skin protection clothing of the fifth embodiment.

Skin protection clothing 29 of FIG. 8 is a further embodiment that is made for adults and children, using non-absorbent two-layer fabric. This will prevent the absorption of beneficial ointment oil 14. By providing a barrier material between the skin and regular clothing, this enables the person to retain beneficial ointment oil 14 on skin for long periods of time, therefore helping in chronic skin conditions such as eczema, psoriasis and other skin ailments. These articles of clothing include but not limited to; shirts, tank tops, shorts, pants, arm bands, wrist bands, knee bands, socks, gloves, hats, and face masks.

Figures 9, 10:
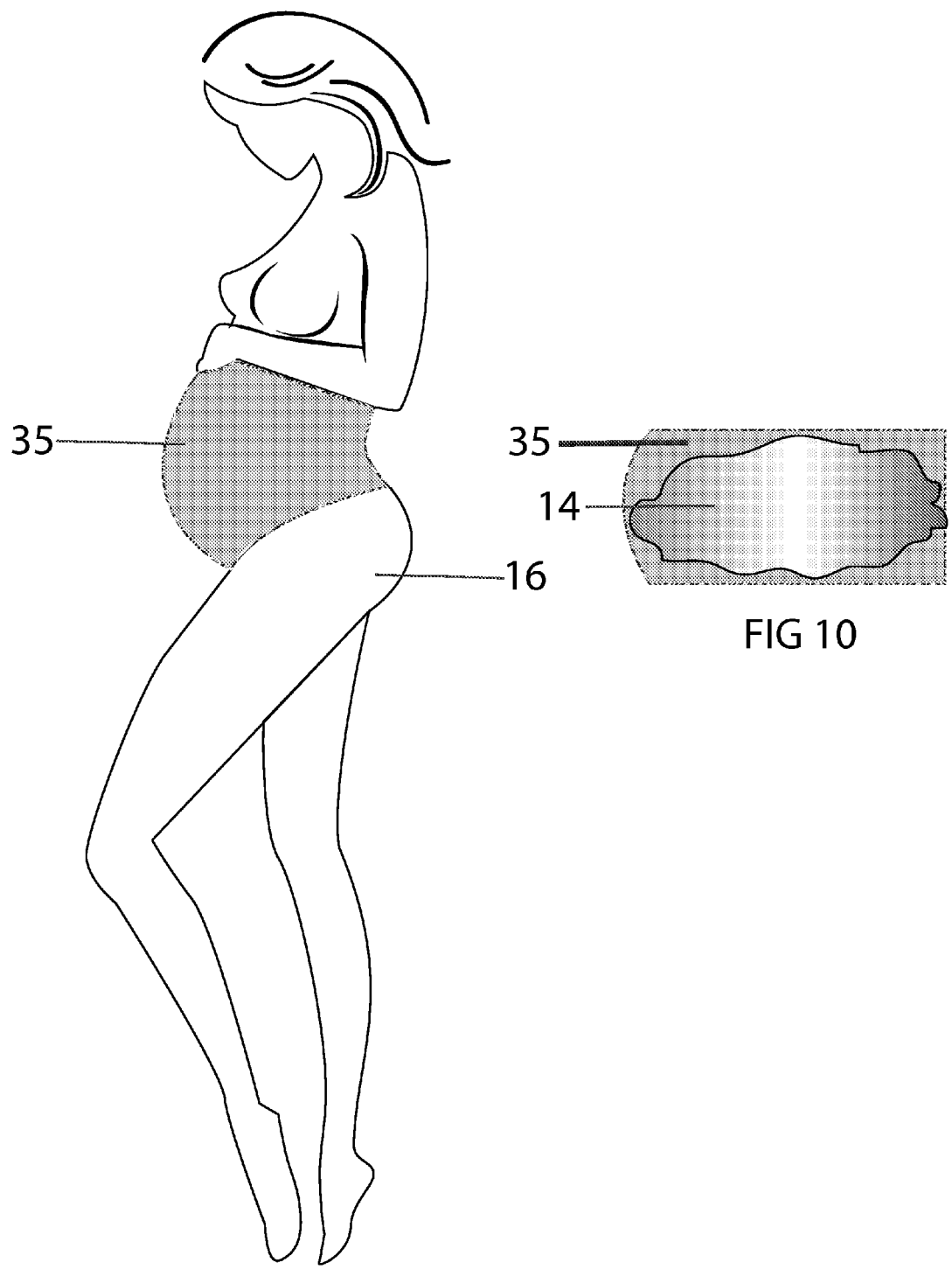
FIG. 9 is a left view of a reusable pregnancy skin wrap of the fifth embodiment.
FIG. 10 is a front view of reusable pregnancy skin wrap of the fifth embodiment.

FIG. 9 and FIG. 10 show a reusable pregnancy skin wrap 35 which may be made out of the same non-absorbent two-layer fabric as the pregnancy skin wrap clothing 20. This embodiment may be to be used in the same manner as the pregnancy skin wrap 22, but instead of being a daily disposable, will be washable and reusable. Ointment oil 14 may be also applied to skin prior to wearing.

In operation, many of the embodiments may assist in ensuring beneficial ointment oil applied to the skin so is not absorbed by regular clothing. By maintaining beneficial natural oils on the stretching pregnant abdomen, thighs, breasts, buttocks and any other area prone to stretch marks, the skin is allowed the proper lubrication needed to stretch and grow without causing stretch marks. This methodology of wearing stretch mark prevention skin wrap clothing in combination with ointment oil also applies to other groups of people including body builders and growing adolescents who are prone to developing stretch marks and would benefit from retaining moisture during times of rapid expansion of the skin.

The invention has now been described in detail for the purposes of clarity and understanding. However, it will be appreciated that certain changes and modifications may be practiced within the scope of the appended claims.

What is claimed is:
1. A method for inhibiting formation of stretch marks on a pregnant woman's abdomen, wherein the method comprises:
   applying an oil to the pregnant woman's abdomen during a second month of pregnancy, wherein the oil is a mixture comprising:
      about 20% olive oil;
      about 20% sweet almond oil;
      about 20% coconut oil;
      about 14% beeswax;
      about 10% avocado oil;
      about 5% cocoa butter;
      about 5% shea butter;
      about 5% tamanu oil; and
      about 1% natural vitamin E;
   putting on a tank top and a pair of shorts, such that the tank top and the pair of shorts covers at least a portion of the oil on the woman's abdomen, wherein:

the tank top and the pair of shorts each comprise two layers of non-absorbent fabric; and
each layer comprises polyester and polyurethane.

\* \* \* \* \*